(12) United States Patent
Hair

(10) Patent No.: US 6,197,037 B1
(45) Date of Patent: Mar. 6, 2001

(54) SURGICAL FASTENER FOR JOINING ADJACENT BONE PORTIONS

(76) Inventor: John Hunter Hair, 122 Haddonfield La., Cary, NC (US) 27513

( * ) Notice: Subject to any disclaimer, the term of this patent is extended or adjusted under 35 U.S.C. 154(b) by 0 days.

(21) Appl. No.: 09/364,253

(22) Filed: Jul. 29, 1999

(51) Int. Cl.⁷ ................................................ A61B 17/58
(52) U.S. Cl. ............................................. 606/151; 606/72
(58) Field of Search ............................... 606/151, 72, 75, 606/69, 70, 71, 86; 24/297, 324, 662

(56) References Cited

U.S. PATENT DOCUMENTS

| | | | | |
|---|---|---|---|---|
| 4,050,184 | * | 9/1977 | Chiari | 446/86 |
| 4,058,909 | * | 11/1977 | Poleri | 434/72 |
| 4,122,583 | * | 10/1978 | Grittner et al. | 24/703.1 |
| 4,176,428 | * | 12/1979 | Kimura | 24/326 |
| 5,456,714 | * | 10/1995 | Owen | 623/1 |
| 5,885,284 | * | 3/1999 | Erico et al. | 606/61 |
| 6,022,351 | * | 2/2000 | Bremer et al. | 606/72 |
| 6,068,631 | * | 5/2000 | Lerch | 606/72 |

* cited by examiner

*Primary Examiner*—Paul J. Hirsch
*Assistant Examiner*—Michael B. Priddy
(74) *Attorney, Agent, or Firm*—Coats & Bennett, PLLC

(57) ABSTRACT

A surgical fastener for joining adjacent bone portions includes a top flange and a bottom flange joined by a rib that together help define two bone receiving cavities. The Respective bone edge portions, such as from an osteotomy cut, are inserted into the bone receiving cavities and gripped by the compressive action between the top flange and the bottom flange. In the installed state, the top flange is disposed on one side of the bone while the bottom flange is disposed on the opposite side of the bone, with the rib disposed between the bone edges. The bone clamp may be a unitary device that is made from a flexible bioresorbable material. Due to its configuration, the bone clamp may be installed without the use of any tools. Further, the bone clamp acts as a temporary fastener in that it dissolves over time, thereby allowing for the bone edges to knit, even in the vicinity of the bone clamp. When installed, the bone clamp has a low profile initially and no long term profile, thereby lessening cosmetic abnormalities.

35 Claims, 6 Drawing Sheets

SURGICAL FASTENER FOR JOINING ADJACENT BONE PORTIONS

FIELD OF THE INVENTION

This invention relates to a surgical fastener for joining two adjacent portions of bone, for example, when replacing a portion of the cranial vault removed during a craniotomy, and a related method of using the surgical fastener.

BACKGROUND OF THE INVENTION

In most neurosurgical and cranial operations, it is necessary to open a large access hole in the skull by forming a segment of the skull, called a bone flap, which is then bent out of the way or broken out from the surrounding skull. To form the bone flap, several holes are typically drilled through the skull, commonly referred to as burr holes. The burr holes are then connected by one or more osteotomy cuts, for example by using a Gigli flexible saw which is passed internally between the burr holes. The saw is then oscillated back and forth to cut the skull along a path connecting adjoining burr holes. The position, number, and size of the burr holes drilled through the skull, as well as the number of connecting osteotomies, is determined by the size, location and geometrical form of the desired bone flap and corresponding access hole. For example, if the bone flap to be removed is a triangular skull cap segment, three holes are preferably drilled at the corner points of the bone flap, connecting osteotomies are made along the sides of the curved triangle delineated by burr holes, resulting in a triangular segment bone flap. The bone flap is subsequently lifted off the underlying dura matter to expose the brain for the further steps of the operation. The bone flap may either be completely removed from the surgical site, or folded back along an uncut edge.

At the end of the procedure, the previously removed bone flap or flaps are repositioned into their original locations, or in different desired locations, relative to the surrounding bone portions. This is typically accomplished in the prior art by drilling pairs of small holes in the surrounding skull bone in several places around the edge of the bone flap. Wire is then carefully threaded through the holes, taking care not to tear the dural tissue covering the brain, then twisted together to secure the edges, the ends tucked into the osteotomy cut opening so that they do not puncture the skin, and the skin then stitched into place over the skull flap. The procedure is complex and time consuming, and there always is the possibility of injuring the dura either by using the high speed drills that are necessary to form the small holes or by the sharp points of the wire engaging the dura.

Other known methods for providing fixation between adjacent bone portions have included the use of metallic plates of varying configurations which are secured across osteotomies or fracture sites by metallic bone screws. Other devices, such as intramedullary nails, have also been used to reduce bone fracture mobility and to improve the relative position of adjacent segments. See for instance U.S. Pat. No. 5,669,912 to Spetzler, U.S. Pat. No. 5,549,620 to Bremer, and U.S. Pat. No. 5,916,217 to Manthrop. The aim of fixation of adjacent bone portions is to immobilize the fracture or osteotomy sites in order to promote localized bone growth in the natural repair of the separation.

A brief survey of prior art methods may be found by looking at patents previously issued on the subject. For instance, U.S. Pat. No. 5,201,737 discloses a flexible plate having a plurality of vanes with holes for receiving bone screws. The plate is placed over a cranial burr hole and adjoining osteotomy lines to provide external fixation of the bone flap to the surrounding cranium. Other external bone plates are shown in U.S. Pat. Nos. 4,651,724; 4,923,471; 5,139,497; 5,372,498; and 5,578,036. All of these plates are designed for external application to fractured bones and require placement of a plurality of screws through the plates and into the bone. Placement of multiple screws through the plates is time consuming, induces additional trauma in drilling the pilot holes for the screws, and may predispose the site to infection.

In spite of the use of a variety of fasteners in surgical procedures, improved techniques are still being sought to secure adjacent portions of bone for healing, particularly for securing bone flaps to the surrounding cranium following a craniotomy.

SUMMARY OF THE INVENTION

The present invention utilizes a surgical fastener, frequently referred to herein as a bone clamp, to join adjacent bone portions. The bone clamp typically includes a top flange and a bottom flange joined by a rib, or rib assembly, that together help define two bone receiving cavities. The edge of each of the adjacent bone portions is inserted into the respective bone receiving cavity and gripped by the compressive action between the top flange and the bottom flange. In the installed state, the top flange is disposed on one side of the bone portions while the bottom flange is disposed on the opposite side of the bone portions, with the rib disposed between the bone edges.

In one preferred embodiment, the bone clamp is a unitary device that is made from a flexible bioresorbable material. Due to its configuration, the bone clamp may be installed without the use of any tools. Further, the bone clamp acts as a temporary fastener in that it dissolves over time, thereby allowing for the bone edges to knit, even in the vicinity of the bone clamp. In addition, due to their flexibility the bone clamps transfer a portion of the radial stress exerted on the bone flap to the bone itself. As the bone clamp dissolves, a greater and greater portion of the radial load is transferred to the bone. It is believed that this stress transferring approach promotes better bone healing than approaches that rely primarily on supporting the stress via a rigid fastener.

Thus, in the preferred embodiments, the bone clamp provides a safe, simple, easy to use fastener for temporarily joining adjacent portions of bone. The bone clamp does not require the use of a drill or screws to install. When installed, the bone clamp has a low profile initially and no long term profile, thereby lessening cosmetic abnormalities.

DETAILED DESCRIPTION

Figure 1:
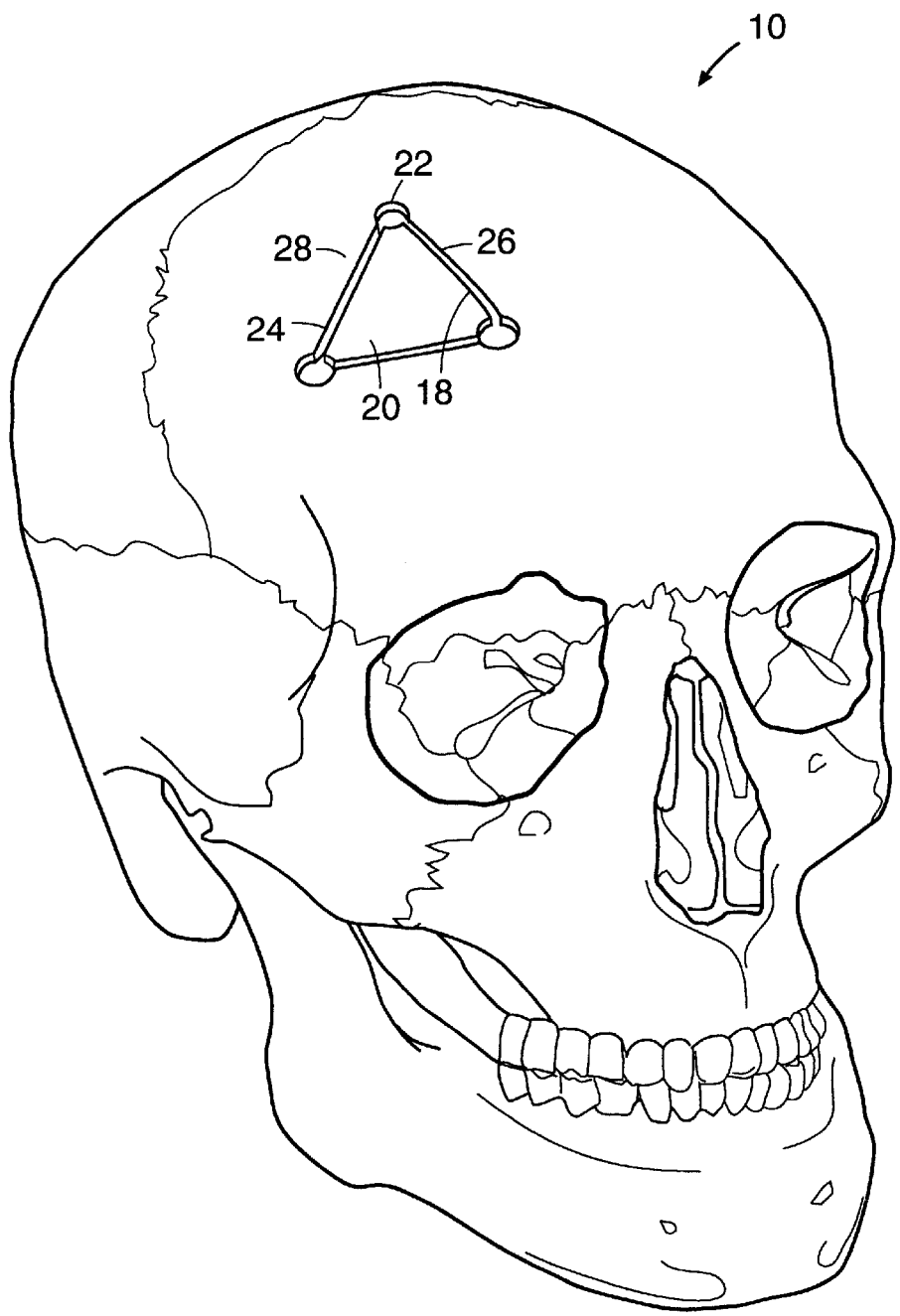
FIG. 1 is representative view of a human head showing one possible location and configuration of a craniotomy bone flap.

For reference, a human skull 10 with a craniotomy bone flap 20 is shown in FIG. 1. The bone flap 20 is defined by three burr holes 22 and the connecting osteotomy cuts 24. As pointed out above, the bone flap 20 need not be of the particular shape shown and may have any number of burr holes 22. On the opposing sides of the osteotomy cuts 24 are the respective bone edge surfaces 18,26 of the bone flap 20 and the surrounding bone 28 of the skull 10, respectively.

Figure 3:
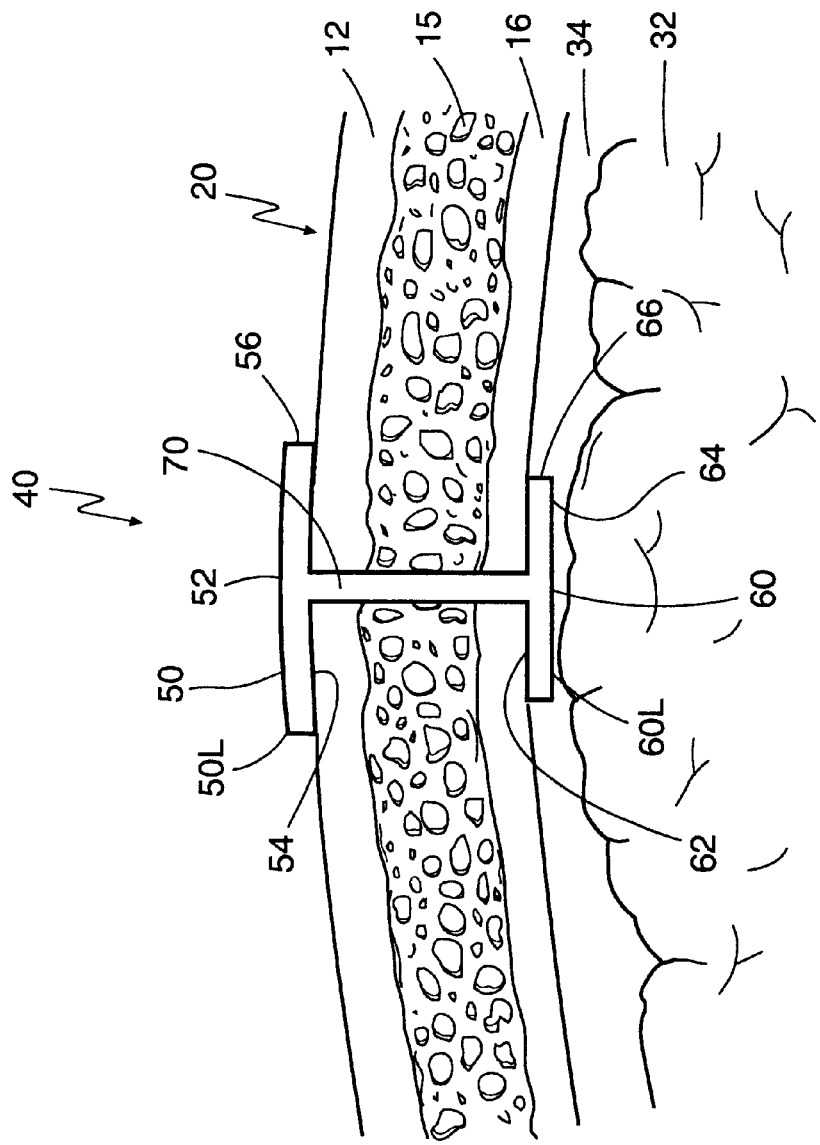
FIG. 3 is a side view of the bone clamp of FIG. 2 in the use state and fully installed in an osteotomy.
Figure 4:
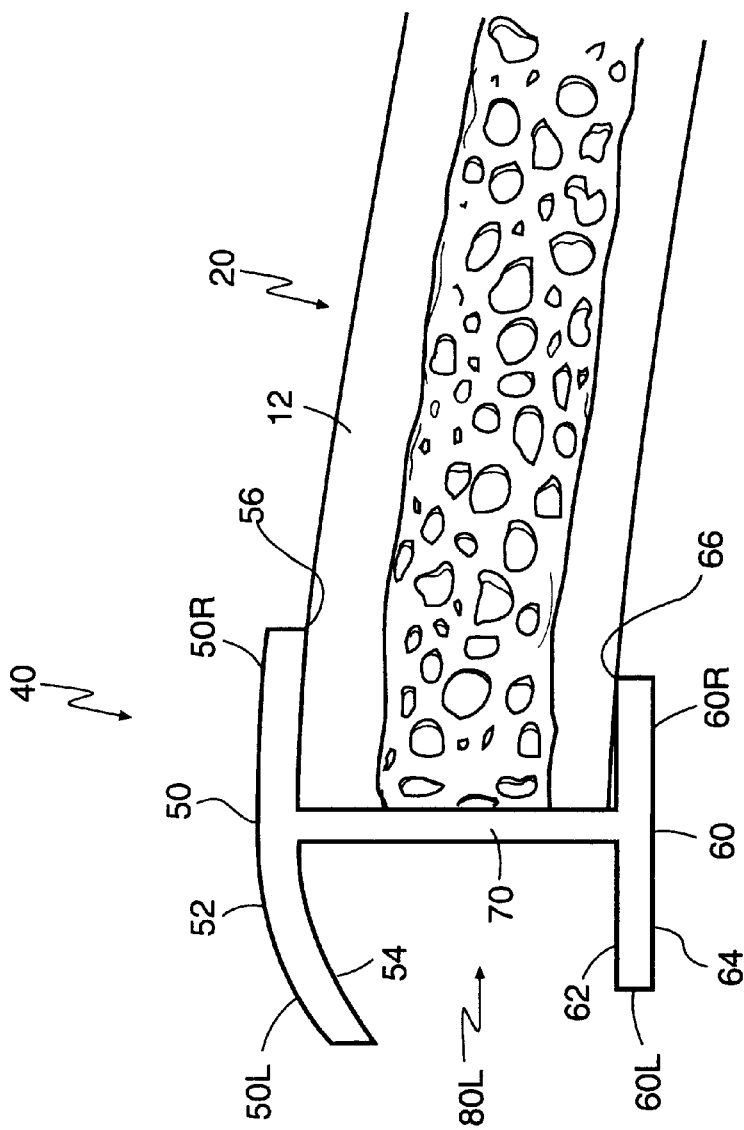
FIG. 4 is a side view of the bone clamp of FIG. 2 installed on a bone flap prior to the full installation of FIG. 3.
Figure 5:
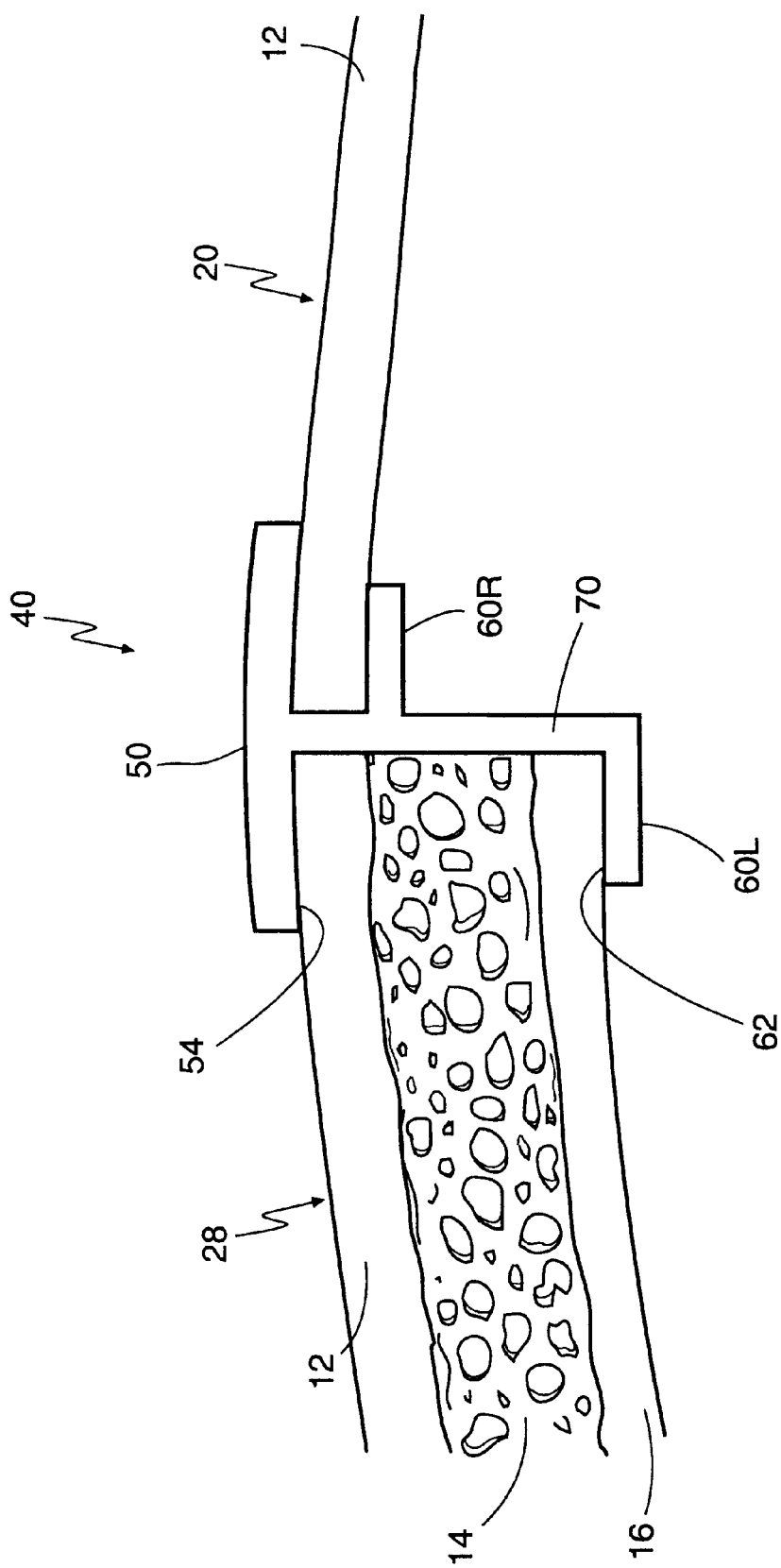
FIG. 5 is a side view of an alternate embodiment of the bone clamp that is adapted for use with adjacent bone sections having differing thicknesses.

The skull 10 and bone flap 20 are typically made from bone that can be considered to have a three layer composition, as shown in FIGS. 3–5. The outermost layer is the outer cortical bone 12 and the innermost layer is the inner cortical bone 16. Between these two relatively stiff layers is a relatively soft middle layer known as the cancellous bone 14. Interior to the inner cortical bone 16 is the cranial cavity 30 housing the brain 32 and its surrounding dura matter 34. While FIG. 1 shows a completely surgically-created bone flap 20, it is to be understood that the bone flap 20, including the burr holes 22 and the osteotomy cut lines 24, may be formed by other means, such as by impact trauma and the like.

The present invention utilizes at least one, and preferably a plurality of, surgical fasteners, typically referred to herein as bone clamps 40, to join together two adjacent portions of bone 20,28. The approach is particularly adapted for securing craniotomy bone flaps 20 to the skull 10, but may be used in other situations where appropriate. The present illustrative discussion will assume that the bone clamp 40 is being used to close a typical triangular craniotomy bone flap 20 having three burr holes 22, one at each apex, connected by thin osteotomy cuts 24 which may be normal to the surface of the skull 10 or at an angle thereto.

Figure 2:
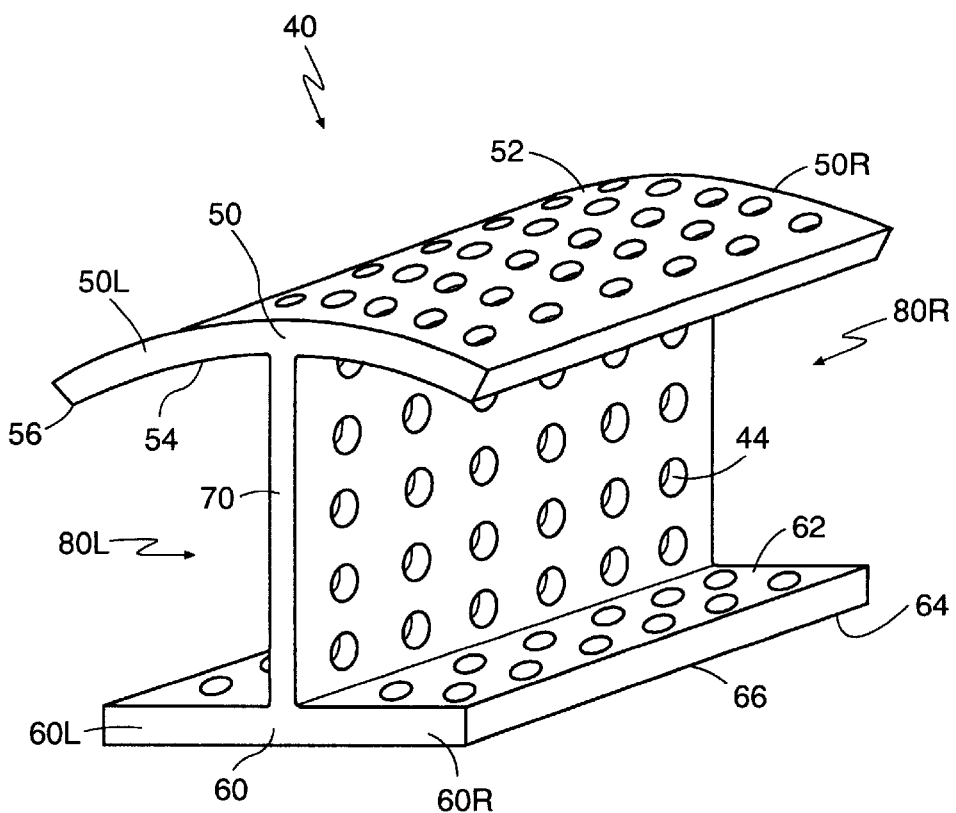
FIG. 2 is a perspective view of one embodiment of a bone clamp of the present invention in a pre-use state.

For the embodiment illustrated in FIG. 2, the bone clamp 40 includes a top flange 50, a bottom flange 60, and an intervening rib 70. The top flange 50 is preferably a generally planar member having a top surface 52, a bottom surface 54, and a peripheral edge 56. While the top flange 50 may be relatively flat, the top flange 50 in the pre-use state (FIG. 2), is preferably slightly curved downwardly so as to be a portion of a cylinder. The top flange 50 is preferably slightly wider than the bottom flange 60 as can be seen in FIG. 3. For purposes of discussion, the top flange 50 may be divided into a left portion 50L and a right portion 50R.

The bottom flange 60 is likewise preferably a generally planar member having a top surface 62, a bottom surface 64, and a peripheral edge 66. Unlike the top flange 50, the bottom flange 60 is preferably relatively flat. Like the top flange 50, the bottom flange 60 may be divided into a right portion 60R and a left portion 60L for purposes of discussion.

The rib 70 links the top flange 50 to the bottom flange 60. Preferably, the rib 70 extends between a center portion of the bottom surface 54 of the top flange 50 to a center portion of the top surface 62 of the bottom flange 60. The rib 70 should be approximately the thickness of the osteotomy cut 24 so as to be able to fit therein, as explained below. While the rib 70 may be joined to the top flange 50 and the bottom flange 60 in any manner, the rib 70 is preferably formed integral to both the top flange 50 and the bottom flange 60 so that the bone clamp 40 is a unitary structure.

The bottom surface 54 of the top flange 50, the rib 70, and the top surface 62 of the bottom flange 60 together help define a left bone receiving cavity 80L and a right bone receiving cavity 80R. While these two cavities 80R,80L may be of different shape, they are preferably mirror images of one another. Preferably, the bone receiving cavities 80L,80R are about 4 to about 12 mm in height, but smaller and larger sizes may be appropriate in some instances, depending on the corresponding bone thickness.

The bone clamp 40 may be formed from a wide variety of relatively flexible materials. For instance, the clamp may be made from thin stainless steel, titanium, or other biocompatible metal or metallic alloy; biocompatible plastic compounds, or other flexible biocompatible materials known in the art. However, the bone clamp 40 is preferably made from a bioresorbable material such as that disclosed in U.S. Pat. No. 5,919,234 to Lemperle et al, which is incorporated herein by reference. To aid in the bioresorption, the material of the bone clamp 40 preferably includes a plurality of pores 44 having a diameter in the range of 20 $\mu$m to 3000 $\mu$m. While not required, the bone clamp 40 is preferably made from a material with a thickness in the range of approximately 0.5 mm to 1 mm, and the flanges 50,60 are optionally a uniform thickness throughout.

Referring to FIG. 3, the bone clamp 40 is installed such that the top flange 50 rests outside the skull 10 and the bone flap 20, the bottom flange 60 is inside, and the rib 70 is in an osteotomy cut 24. FIG. 3 shows that the bone edge 18 of the skull 10 fits into the right bone receiving cavity 80R while the bone edge 26 of the bone flap 20 fits into the left bone receiving cavity 80L. The two bone edges preferably rest against the rib 70 so that the rib 70 fills that portion of the osteotomy cut 24 in the vicinity of the bone clamp 40. In the fully installed position, the edge 56 of the top flange 50 should tightly engage the outer surface of the corresponding bone, and preferably the entire bottom surface 54 of the top flange 50 lies tight against the outer surface of the nearby bone. A tighter gripping action for this installed, or use state, condition may be achieved by configuring the bottom surface 54 of the top flange 50 with a downwardly curving profile, as shown in FIG. 2. When in installed, the curving profile should be flattened-out, at least partially, as shown in FIG. 3. Likewise, the edge 66 of the bottom flange 60 should tightly engage the corresponding inner surface of the bone. While the top surface 62 of the bottom flange 60 may also be curved to promote the gripping action, the top surface 62 may also be straight, or slightly curved outwardly, to better conform to the inner surface of the nearby bone.

The use of the bone clamp 40 may be illustrated in the context of the closure of the fully removed three-sided craniotomy described above. When the craniotomy is ready for closure, a bone clamp 40 is positioned along one edge 26 of the bone flap. The bone edge 26 of the bone flap 20 is inserted into one of the bone receiving cavities 80L, 80R, for purposes of illustration the right bone receiving cavity 80R. To do so, the left portion 50L of the top flange 50 and the left portion 60L of the bottom flange 60 are pressed towards one another by hand, thereby deflecting the left portion 50L of the top flange 50 downwardly in the orientation shown in FIG. 4. This action forces the right portion 50R of the top flange 50 away from the right portion 60R of the bottom flange 60, thereby expanding the right bone receiving cavity 80R, and optionally deflects the rib 70. The bone clamp 40 is then pushed onto the bone flap 20. When the left portion of the bone clamp 40 is released, the right portion 50R of the top flange 50 springs back towards the bottom flange 60, thereby gripping the bone edge 26 between the top flange 50 and the bottom flange 60. Thereafter, additional bone clamps 40 are optionally installed at other locations around the periphery of the bone flap 20. Preferably, the two bone clamps 40 are arranged on each peripheral side of the bone flap 20, excluding one side.

Thereafter, the bone flap 20, with the bone clamps 40 attached, is positioned in the corresponding opening of the skull 10 and the bone edge 18 of the skull 10 is inserted into the open bone receiving cavities 80R,80L of the bone clamps 40 (for purposes of illustration, the left bone receiving cavities 80L). In order to facilitate this insertion, at least the left portion 50L of the top flange 50 is optionally longer than the corresponding portion 60L of the bottom flange 60 so that the top flange 50 overhangs by some small amount, such as 1 mm. Of course, in order to facilitate ease of use, both the left portion 50L and the right portion 50R of the top flange 50 may optionally be longer in such a manner. The lip formed by the overhang may then be pressed against the upper surface of the bone, thereby deflecting the left portion 50L of the top flange 50 and enlarging the left bone receiving cavity 80L. At the same time, the bone flap 20 is urged downwardly and forward until the left bone receiving cavity 80L slips over the bone edge 18 of the skull 10. The process is then repeated for the other bone clamps 40. Optionally, all the bone clamps 40 along one peripheral edge of the bone flap 20 may be attached to the skull 10 at one time, and then another edge attached, and so forth, or all the bone clamps 40 may be attached at essentially the same time.

It should be noted that to temporarily increase the ductility of the bone clamp 40, the bone clamp 40 may be optionally heated prior to application. For instance, the bone clamp 40 may be placed in 140–160° F. water for five to ten seconds and then installed on the bone flap 20.

After the bone flap 20 is attached to the skull via the bone clamps 40, the remaining side of the bone flap 20 is secured in a conventional manner. For instance, the remaining burr hole 22 may be covered using the bone fixator disclosed in U.S. Pat. No. 5,578,036 to Stone et al. However, the bone flap 20 is preferably secured by using the expanding closure device disclosed in Applicant's co-pending U.S. patent application Ser. No. 09/292,286, which is incorporated herein by reference. The expanding closure device is preferred, among other reasons, because it applies lateral pressure against the bone flap, thereby squeezing the ribs 70 of the bone clamps 40 between the respective bone edges 18,26. After securing the bone flap 20, the surgical operation is completed in the normal fashion.

The present invention is useful for joining adjacent sections of bone. Such adjacent sections typically do not overlap each other, but instead either abut or almost abut one another. Of course, there may be some small amount of overlap if, for instance, the osteotomy cut 24 defining the boundary between the portions 20,28 is made at an angle that is offset from normal to the bone surface. However, it is intended that the adjacent portions of bone have their corresponding bone edges 18,26 lying generally along a lateral plane, rather than substantially vertically offset from one another.

The description above has used directional terms such as downwardly, upwardly, left, right, and the like for convenience to describe the present invention and its parts as oriented in the drawings. However it is to be understood that such terms are not intended to be limiting since such invention may obviously be disposed in different orientations when in use.

Further, while the description above has assumed that both bone portions 20,28 being joined have three layers, 12,14,16 such is not required. For instance, the bone clamp 40 shown in FIG. 5 is specially adapted for use where the inner two layers 14,16 of the bone flap 20 have been removed, perhaps for grafting elsewhere. The bottom flange 60 shown in FIG. 5 has a right portion 60R offset from its companion left portion 60L, thereby adjusting the size of the right bone receiving cavity 80R to readily accept and grip only the outer cortical bone 12. The bone clamp 40 of FIG. 5 is obviously not readily reversible, but such a configuration may be appropriate in some situations.

The rib 70 shown in FIG. 2 is generally planar; however, such a shape is not required. Indeed, a wide variety of shapes may be appropriate, including slightly curved, rippled, etc. One common characteristic of the rib 70 shapes is that they are radially asymmetric, meaning that they do not have the same dimensions in all "horizontal" radial directions. In simple terms, the rib 70 may have any non-circular overall cross-section. Further, while the rib 70 of FIG. 2 is a unified structure, this is not required. For instance, the rib 70 may be composed of multiple column-like structures, although this configuration may be less suitable than the structure shown in FIG. 2. The "horizontal" cross-section of such a multiple structure rib 70 would be that of the overall rib 70 including all the components (e.g. column-like structures) thereof.

The flanges 50,60 of FIG. 2 are shown as being generally rectangular; however other shapes may be used. For instance, the flanges 50,60 may have an overall contoured shape with a plurality of finger like projections extending laterally outward. However, flanges 50,60 having a relatively simple shape with a straight peripheral edges 56,66 may be easier to use.

Figure 6:
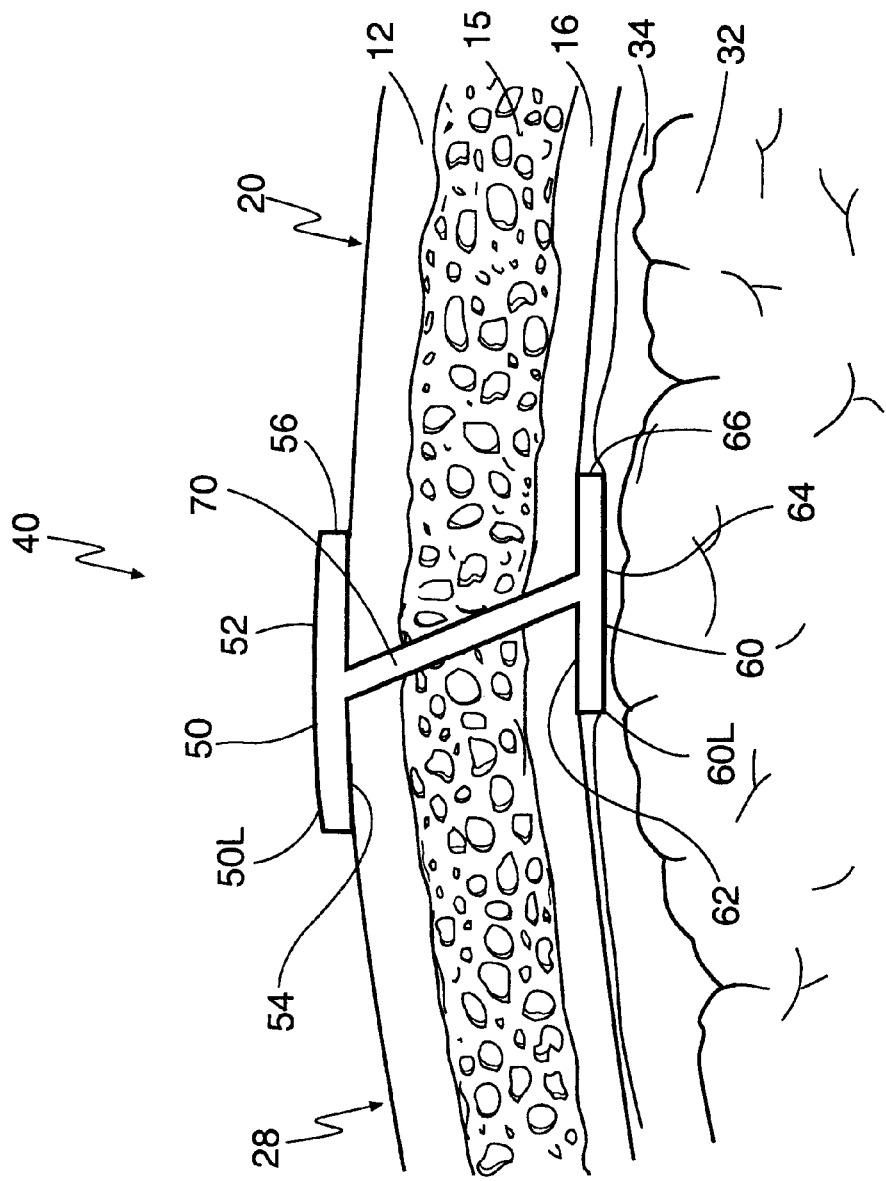
FIG. 6 is a side view of another alternate embodiment of the bone clamp that is adapted for use with slanted osteotomy cuts.

The rib 70 of FIG. 2 is disposed generally perpendicular to the flanges 50,60; however, this is not required. For instance, the bone clamp 40 of FIG. 6 may be advantageously employed when the osteotomy cuts 24 defining the boundary between the bone portions 20,28 is made at an angle that is offset from normal to the bone surface. In order to accommodate such angled osteotomy cuts 24, the angle between the central portion of the rib 70 and each flange 50,60, may be varied within approximately ±45°, and more preferably ±30°, from normal. While not shown in FIG. 6, the length of the respective flange portions 50L,50R,60L, 60R may be adjusted to allow for proper sizing of the bone receiving cavities 80L,80R, such as by lengthening flange portions 60L and 50R.

The preferred embodiments of the bone clamp 40, or bone fastener, of the present invention greatly facilitate proper healing of the bone portions joined together thereby. The bone clamps 40 may be installed by hand without any special tool. Further, no drilling or screwing is required. More importantly, the bone clamps 40 present a very low profile, and after time with the preferred bioresorbable material, present no profile, thereby lessening cosmetic abnormalities. In addition, due to their flexibility, the bone clamps 40 transfer a portion of the radial stress exerted on the bone flap 20 to the surrounding bone 28. As the bone clamp 40 dissolves and the osteotomy cut 24 heals, a greater and greater portion of the load is transferred to the bone via the osteotomy cut 24. It is believed that this stress transferring approach promotes better bone healing than approaches that rely primarily on supporting the stress via a rigid fastener. Thus, in the preferred embodiments, the fastener is only temporary.

The present invention may, of course, be carried out in other specific ways than those herein set forth without departing from the spirit and essential characteristics of the invention. The present embodiments are, therefore, to be considered in all respects as illustrative and not restrictive, and all changes coming within the meaning and equivalency range of the appended claims are intended to be embraced therein.

What is claimed is:

1. A surgical fastener for joining at least two adjacent bone portions, the bone portions having respective exterior and interior surfaces, comprising:

a first flange and a flexible second flange spaced from said first flange;

a radially asymmetric rib assembly linking said first flange to said second flange;

first and second bone receiving cavities defined by said first flange and said second flange and disposed on opposing sides of said rib, said bone receiving cavities adapted to each engage the interior and exterior surfaces of the bone portions; and wherein said first flange, said second flange, and said rib assembly are made from a flexible bio-resorbable material.

2. The fastener of claim 1 wherein said fastener is unitary.

3. The fastener of claim 1 wherein said first flange and said second flange each include a plurality of holes.

4. The fastener of claim 1 wherein said rib assembly includes a generally planar rib.

5. The fastener of claim 1 wherein said rib assembly is disposed generally normal to said first flange.

6. The fastener of claim 4 wherein said second flange and said rib assembly are of substantially the same width as measured along the direction of the interface between said bone portions.

7. The fastener of claim 1 wherein said rib assembly is disposed generally at an angle of between 5 and 45 degrees with respect to normal from said first flange.

8. The fastener of claim 1 wherein said first flange is disposed proximate said interior surface and said second flange is disposed proximate said exterior surface and said first flange and said second flange cooperate to grip the bone portions therebetween.

9. The fastener of claim 8 wherein said first flange and said second flange grip the bone portions therebetween without penetrating said bone portions.

10. The fastener of claim 1 wherein said first flange has a dull perimeter edge and wherein said second flange has a dull perimeter edge.

11. The fastener of claim 1 wherein said fastener has a pre-use state and a use state and wherein, in said pre-use state, said second flange has a generally curved surface bounding at least one of said bone receiving cavities.

12. The fastener of claim 1 wherein:

a) said fastener has a pre-use state and a use state and wherein, in said pre-use state, said second flange has a generally curved surface bounding at least one of said bone receiving cavities;

b) said first and second flanges have substantially uniform respective thicknesses and respective dull perimeter edges;

c) said second flange is larger than said first flange as measured along the direction perpendicular to the interface between the bone portions;

d) said first and second bone receiving cavities are substantially identical;

e) said rib assembly includes a generally planar rib; and f) said fastener is unitary and made from a flexible bio-resorbable material.

13. A flexible surgical fastener for joining at least two adjacent bone portions, the bone portions having respective exterior and interior surfaces, comprising:

a) a first flange and a flexible second flange spaced from said first flange;

b) a rib linking said first flange to said second flange;

c) first and second bone receiving cavities defined by said first flange and said second flange and disposed on opposing sides of said rib and adapted to engage the interior and exterior surfaces of the bone portions, respectively; and d) wherein said first flange, said second flange, and said rib are made from a flexible bio-resorbable material.

14. The fastener of claim 13 wherein said fastener is unitary.

15. The fastener of claim 13 wherein said rib is generally planar.

16. The fastener of claim 15 wherein said second flange and said rib are of substantially the same width as measured along the direction of the interface between said bone portions.

17. The fastener of claim 13 wherein said first flange has a dull perimeter edge and wherein said second flange has a dull perimeter edge.

18. The fastener of claim 13 wherein said fastener has a pre-use state and a use state and wherein, in said pre-use state, said second flange has a generally curved surface bounding at least one of said bone receiving cavities.

19. The fastener of claim 13 wherein said first flange is disposed proximate said interior surface and said second flange is disposed proximate said exterior surface and said first flange and said second flange cooperate to grip the bone portions therebetween.

20. The fastener of claim 19 wherein said first flange and said second flange grip the bone portions therebetween without penetrating said bone portions.

21. The fastener of claim 13 wherein:

a) said fastener has a pre-use state and a use state and wherein, in said pre-use state, said second flange has a generally curved surface bounding at least one of said bone receiving cavities;

b) said first and second flanges have substantially uniform respective thicknesses and respective dull perimeter edges;

c) said second flange is larger than said first flange as measured along the direction perpendicular to the interface between the bone portions;

d) said first and second bone receiving cavities are substantially identical;

e) said rib is generally planar; and f) said fastener is unitary.

22. A flexible surgical fastener for joining adjacent bone portions, the bone portions having respective exterior and interior surfaces, comprising:

a first flange and a flexible second flange spaced from said first flange;

first and second bone receiving cavities defined by said first flange and said second flange and adapted to engage the exterior and interior surfaces of the bone portions;

means for connecting said first flange to said second flange; and wherein said first flange, said second flange, and said means for connecting are made from a flexible bio-resorbable material.

23. The fastener of claim 22 wherein said fastener is unitary.

24. The fastener of claim 22 wherein said first flange is disposed proximate said interior surface and said second flange is disposed proximate said exterior surface and said first flange and said second flange cooperate to grip the bone portions therebetween without penetrating said bone portions.

25. The fastener of claim 22 wherein said fastener has a pre-use state and a use state and wherein, in said pre-use state, said second flange has a generally curved surface bounding at least one of said bone receiving cavities.

26. The fastener of claim 23 wherein:
   said fastener has a pre-use state and a use state and wherein, in said pre-use state, said second flange has a generally curved surface bounding at least one of said bone receiving cavities;
   said first and second flanges have substantially uniform respective thicknesses and respective dull perimeter edges;
   said second flange is larger than said first flange as measured along the direction perpendicular to the interface between the bone portions;
   said first and second bone receiving cavities are substantially identical;
   said connecting means includes a generally planar rib;
   wherein said fastener is unitary and made from a flexible bio-resorbable material.

27. A method of joining first and second bone portions using a temporary fastener, comprising:
   a) forming at least one osteotomy cut line substantially defined by first and second bone edge portions adjacent to each other on along at least one edge;
   b) providing a flexible fastener having at least a first flange, a second flange, a rib linking said first flange to said second flange, first bone receiving cavity, a second bone receiving cavity;
   c) installing said flexible fastener between said first and second bone edge portions such that said first flange is disposed interior to said bone portions and said second flange is exterior to said bone portions; and
   d) thereafter allowing said fastener to dissolve over an extended period of time.

28. The method of claim 1 wherein said installing further includes thereafter positioning the second bone edge portion in said second bone receiving cavity and gripping said second bone edge portion between said first flange and said second flange.

29. The method of claim 27 wherein said installing includes bringing said first and second bone edge portions into contact with said rib.

30. The method of claim 27 wherein said rib occupies substantially all the space between said first bone edge portion and said second bone edge portion in the immediate area of said flexible fastener.

31. The method of claim 27 wherein said flexible fastener is made from a bio-resorbable material and further comprising allowing said fastener to remain in place until said fastener dissolves.

32. The method of claim 27 wherein said flexible fastener is unitary.

33. The method of claim 27 wherein said extended period of time is greater than ninety days.

34. The method of claim 27 wherein said installing is accomplished without the use of tools.

35. The method of claim 27 wherein said installing includes:
   a) deflecting said first flange proximate the second bone receiving cavity so as to shrink the second bone receiving cavity and thereby expand the first bone receiving cavity;
   b) positioning said first bone edge portion within said first bone receiving cavity and releasing said first flange and thereby gripping said first bone edge portion between said first flange and said second flange.

* * * * *